United States Patent [19]
Härtl

[11] Patent Number: 5,124,555
[45] Date of Patent: Jun. 23, 1992

[54] HIGH PRESSURE WINDOW ASSEMBLY

[75] Inventor: Hans-Georg Härtl, Karlsruhe, Fed. Rep. of Germany

[73] Assignee: Hewlett-Packard Company, Palo Alto, Calif.

[21] Appl. No.: 637,031

[22] Filed: Jan. 3, 1991

[51] Int. Cl.⁵ .................. G01N 21/09; G01N 21/05
[52] U.S. Cl. .................... 250/373; 250/343; 356/246
[58] Field of Search ............... 356/246; 250/373, 343

[56] References Cited

U.S. PATENT DOCUMENTS

| | | | |
|---|---|---|---|
| 4,872,753 | 10/1989 | Danigel et al. | 356/246 |
| 4,997,275 | 3/1991 | Gaucher et al. | 356/72 |
| 5,073,346 | 12/1991 | Scott et al. | 422/70 |

OTHER PUBLICATIONS

H. D. Stromberg and R. N. Schock, "A Window Configuration for High Pressure Optical Cells." *The Review of Scientific Instruments*, vol. 41, No. 12 (Dec. 1970?) pp. 1880–1881.

R. R. Gordon, M.A., Ph.D., and H. Powell, Ph.D., "Variable Path-Length Cell for the Measurement of the Absorption of Liquids in the Infra-Red Region of the Spectrum." *Journal of Scientific Instruments*, vol. 22 (Jan. 1945) pp. 12–14.

Primary Examiner—Constantine Hannaher

[57] ABSTRACT

This invnetion relates to a high pressure sealed window assembly which does not result in substantial shear forces being applied to the window, and in particular to such a window assembly for transmitting ultraviolet light in high pressure chromatographic detectors. The window has opposed faces through which light is transmitted and angled surfaces extending toward each other away from corresponding points on the outer edge of the opposed surfaces. Sealing rings, preferably shaped to conform to the shape of the angled surfaces, bear against such surfaces and precompression forces are applied through the sealing rings to precompress the window, preferably over substantially its entire volume. When pressure is applied to one face of the window, the precompression forces must be overcome before such pressure can result in shear forces being developed in the window. Thus, by sufficiently precompressing the window, shear stresses can either be eliminated or reduced to a level which does not pose a danger to the window.

15 Claims, 2 Drawing Sheets

HIGH PRESSURE WINDOW ASSEMBLY

FIELD OF THE INVENTION

This invention relates to windows for high pressure applications and more particularly to a high pressure sealed window assembly which is adapted to transmit ultraviolet light.

BACKGROUND OF THE INVENTION

In chromatographic detectors and numerous other applications, a window is required to pass light radiation between a chamber which is either pressurized or evacuated and an environment which is at atmospheric pressure or at some other pressure different from that of the chamber. This results in a relatively large pressure gradient across the window.

While windows for such applications may have curved faces and act as lenses to focus light radiation passing therethrough, typically, light radiation is to pass through the window undistorted. For this, it is necessary that the window have substantially flat surfaces which are oriented substantially perpendicular to the direction of the radiation. Typically, such windows are of the type shown in FIG. 1 where the window assembly 8 has a window 10 with a substantially rectangular cross section, the window being held, for example, between an outer sealing ring 12 and an inner sealing ring 14. Sealing rings 12 and 14 are held in place by, for example, a retaining ring 16 and are generally pressed between plates or other means utilized to precompress the sealing rings so that the seal is maintained when a pressure differential is applied across the window 10. This is necessary because, assuming pressure is applied to the window in the direction of arrow 18, window 10 moves slightly in response to the pressure, pressing against seal 12 while the pressure against seal 14 is reduced. Without precompression, seal 14 would fail, resulting in the potential loss of fluid or gas being retained to the right of window 10.

The configuration shown in FIG. 1 works reasonably well so long as the pressure differential across window 10 is not too great. However, for some applications, such as in a detector cell for super critical fluid chromatography (SFC), the pressure differential across the window may be 6,000 psi or more. In such applications, the window 10 is typically of a material such as quartz or fused silica which is transparent to ultraviolet light. Unfortunately, such materials have far greater resistance to compression stresses than to shear stresses. At high pressure, shear stresses may occur in such windows, causing potential failure thereof in at least two ways.

First, in order to prevent seal failure, it is necessary that the window assembly 8 have high precompression forces applied thereto. Theoretically, such forces would be provided uniformly around the perimeter of window 10, which window is typically round. However, it is difficult to avoid small irregularities in both the window 10 and in pressure plates utilized to apply the precompression forces. These small irregularities result in larger pressures being applied to some portions of the window perimeter than other portions and thus in shear stresses being applied to window 10. In applications where high precompression forces are required, such shear stresses can result in failure of window 10 during the precompression operation or thereafter.

Assuming the window 10 survives the precompression operation, when a pressure differential is applied across the window, the forces 18 are applied to the portion of window 10 inside sealing rings 12 and 14. These forces are countered by forces applied by sealing ring 12 to the outer periphery of the window. This results in substantial shear stresses being applied to the window which, at high pressure, can result in failure of the window.

Failure of the window 10 in a window assembly 8 being used in a piece of equipment such as a chromatographic detector can result in the loss of material being tested and, more important, result in expensive repairs and in the expense involved in what may be substantial equipment down time.

It is, therefore, desirable that windows and window seals be provided for high pressure applications which can withstand high precompression forces and high pressure differentials across the window without resulting in excessive shear stresses being applied to the window. In particular, it would be desirable if the window and seals could be designed such that most of the forces applied to the window would be compressive forces or stresses rather than shear stresses.

SUMMARY OF THE INVENTION

It is, therefore, a primary object of this invention to provide an improved window assembly for high pressure light transmitting applications which does not result in substantial shear forces being applied to the window and, in particular, to develop such a window assembly for transmitting ultraviolet light in high pressure chromatographic detectors.

In accordance with the above, this invention provides a window assembly for transmitting predetermined light radiation in applications where a substantial pressure differential exists between the environment separated by the window. A window is provided of a material which is substantially transparent to the light radiation and which can withstand greater compression stresses than shear stresses. The window has opposed surfaces in the area thereof through which the radiation is to pass which may either be substantially flat and oriented substantially perpendicular to the direction of radiation transmission or may be curved to focus the light. The opposed surfaces preferably have a generally cornerless shape. The window also has angled surfaces extending toward each other from corresponding points on outer edges of the opposed surfaces, each of the angled surfaces extending at a predetermined angle to the corresponding opposed surface. A sealing ring bears against each of the angled surfaces and a means is provided for applying a precompression force to the sealing rings sufficient to normally maintain the window sealed when the pressure differential exists thereacross. This also results in precompression of the window, preferably over substantially its entire volume.

For preferred embodiments of the invention, the opposed surfaces are flat surfaces having a generally circular shape and each of the angled surfaces has a generally conical shape with the conical shape being truncated at the flat surfaces. The sealing rings are also preferably formed with an angled surface which substantially matches the angled surface of the window in contact therewith so that the sealing contact between the window and sealing ring is optimized. The predetermined angle at which the angled surface extends from the flat surface may be substantially constant along the extent of each angled surface and would preferably be approximately 45 degrees so that forces applied normal to the angled surface are directed substantially toward the center of the window. To a lesser extent, this objective may be substantially achieved where the predetermined angle changes along the extent of each angled surface, and in particular where the window has a spherical shape with the flat surfaces being formed on opposite sides of the spherical window, resulting in the angled surfaces being curved.

The foregoing and other objects, features and advantages of the invention will be apparent from the following more particular description of preferred embodiments of the invention as illustrated in the accompanying drawings.

IN THE DRAWING

DETAILED DESCRIPTION

Figure 2:
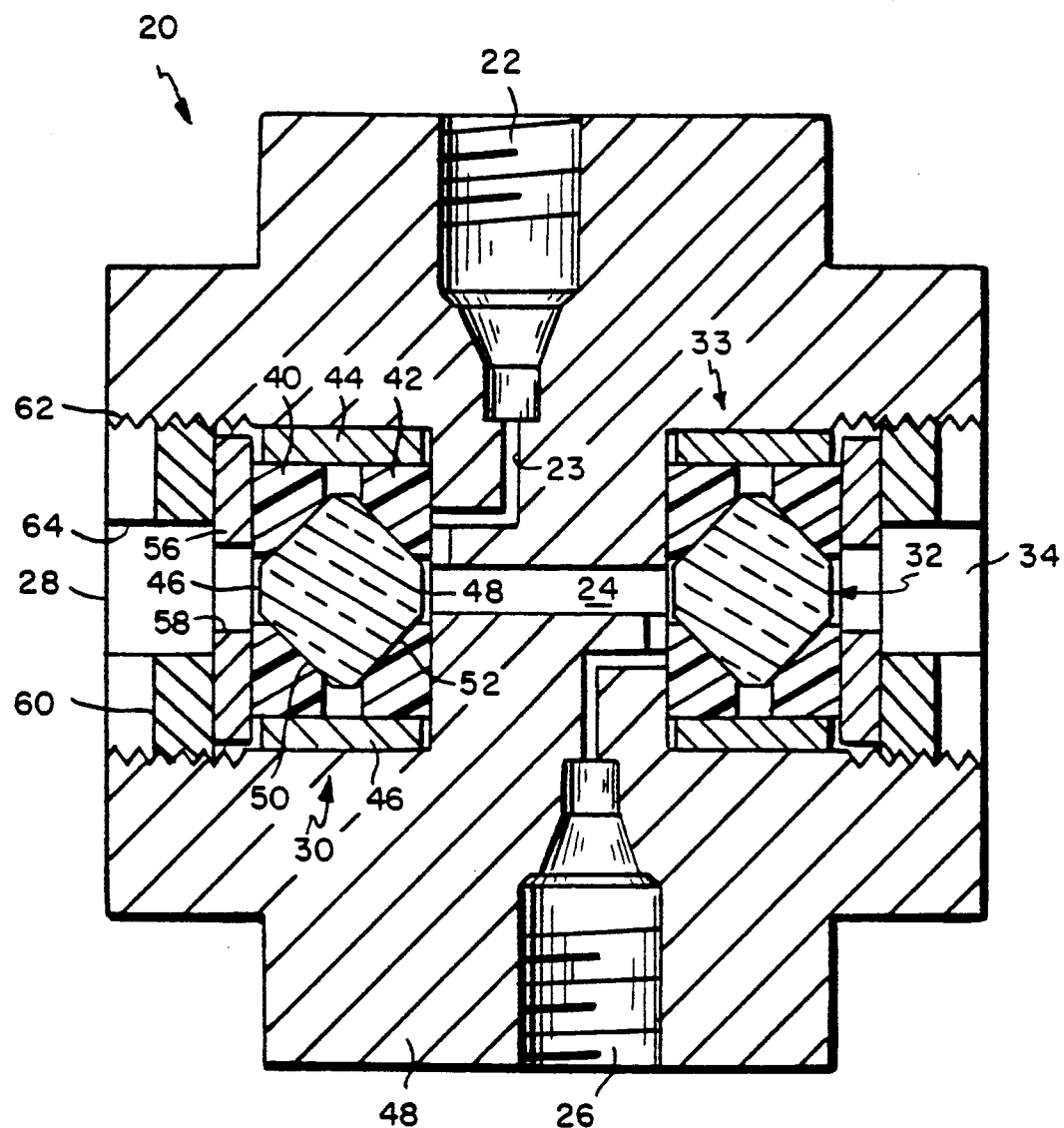
FIG. 2 is a cutaway side view of a portion of a chromatographic detector employing window assemblies in accordance with the teachings of this invention.

FIG. 2 shows a high pressure chromatographic detector employing the window construction of this invention. The detector 20 may, for example, be a super critical fluid chromatography detector (SFC). In such chromatographs, a fluid "mobile phase" is employed as a carrier, the substance to be analyzed being preferably initially separated and then fed through the SFC detector in the mobile phase. The mobile phase carrying the substance to be analyzed is introduced under high pressure into channel 22 and flows through channels 22 and 23 to a pressurized analyzing area or chamber 24. The fluid then flows through this chamber and out through exit channel 26.

Figure 1:
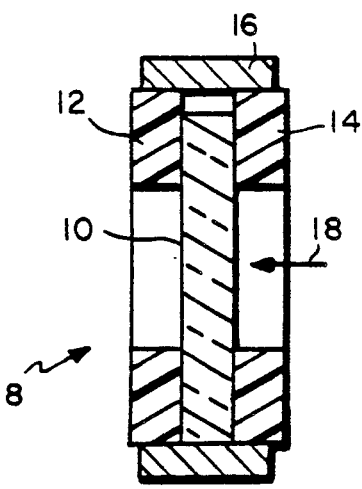
FIG. 1 is a cutaway side view of a single window of a prior art window assembly.

The fluid while in pressurized chamber 24 has ultraviolet light passed therethrough. In particular, ultraviolet light from a source (not shown) enters opening 28 in housing 48, and is passed through window assembly 30 to chamber 24. In chamber 24, some of the ultraviolet light is selectively absorbed and the remaining ultraviolet light passes through exit window 32 of exit window assembly 33 and exit opening 34 to a suitable UV detector (not shown). Since the ultraviolet light absorption of the mobile phase fluid is known or initially determined, the additional absorption by the substance being carried by the mobile phase can be determined and utilized to characterize the substance and/or the concentration of the substance. Detectors of the type shown in FIG. 2 with windows of the type shown in FIG. 1 are known in the art, the Hewlett-Packard 1050 multiwavelength detector and 1050 variable wavelength detector being examples of such detectors. However, such windows have only been used in liquid chromatography (LC) detector where the pressures required are far lower than for SFC detectors.

Since, as previously indicated, the pressure in chamber 24 for SFC applications may approach 6000 psi, or possible more, and since openings 28 and 34 are substantially at atmospheric pressure, a large pressure differential exists across window assemblies 30 and 33. In accordance with the teachings of this invention, the window assemblies are specially designed to operate in such high pressure environments without leakage and without breakage or other failure of the quartz window.

Figure 3:
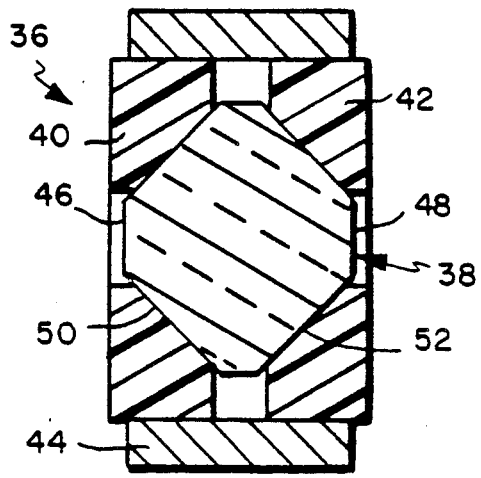
FIG. 3 is an enlarged cutaway side view of a single window assembly of the type shown in FIG. 2.
Figure 4:
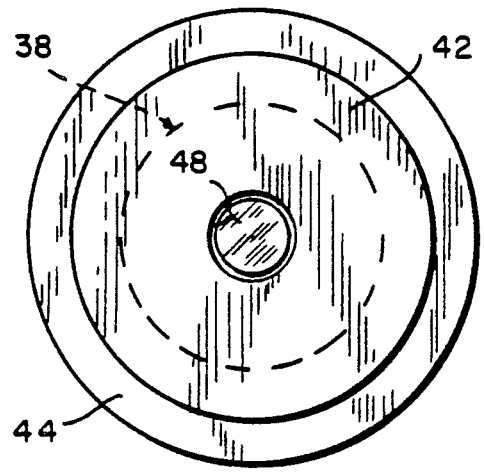
FIG. 4 is a front view of the window assembly shown in FIG. 3.

The window assemblies 30 and 33 are identical and enlarged views of such window assemblies are shown in FIGS. 3 and 4.

Window assembly 36 has a window 38 of quartz, fused silica, sapphire or other suitable material which is mounted between an outer sealing ring 40 and an inner sealing ring 42. The window and seals are retained within a metallic ring 44 with the assembly of parts 38, 40, 42 and 44 being mounted within a window opening 46 (FIG. 2) formed in housing 48 of chromatographic detector 20. Ring 44 functions primarily to make the window assembly easier to install and remove.

Referring both to FIGS. 3 and 4, it is seen that window 38 has a pair of flat, circular surfaces on opposed faces 46 and 48 thereof through which the ultraviolet light passes. These faces are substantially perpendicular to the direction in which the light travels. Angled surfaces 50 and 52 extend toward each other at a selected angle from faces 46 and 48, respectively. The surfaces 50 and 52 each form a truncated cone. The angle at which the surfaces 50 and 52 extend from their respective faces 46 and 48 is preferably approximately 45 degrees. As will be discussed in greater detail later, this angle results in forces applied to the window 38 being directed substantially toward the center of the window, minimizing shear stresses developed in the window. Depending on the thickness of window 38, a cylindrical face may exist around the center of the window as shown in FIG. 3. A typical thickness for window 38 might be approximately 5 mm.

Sealing rings 40 and 42 are either initially formed or machined to have conical surfaces at substantially the same angles as the surfaces 50 and 52, which surfaces are in contact with the corresponding window surfaces. This maximizes the area of contact between window 38 and the sealing rings and thus enhances the seal formed between these elements under varying pressure conditions. The remaining sides of the sealing rings may also be machined to conform to the shape of the element which they are in contact with. Alternatively, the rings may initially have a square cross section with a corner being machined off the cross section as shown to conform to the surfaces 50 and 52.

Once the window assemblies 30 or 33 are installed in the corresponding opening 46, a pressure plate 56, FIG. 2, is positioned for window 30 in opening 28 against sealing ring 40. Plate 56 has an opening 58 formed therein to permit ultraviolet light to pass to surface 46. A second plate 60 having screw threads 62 on the outer edge thereof bears against plate 56. Plate 60 may, for example, have an opening 64 formed therein which permits ultraviolet light to pass therethrough to opening 58. Opening 64 may be hex-shaped to permit a suitable wrench to be inserted therein or a screwdriver slot may be provided in plate 60 to permit plate 60 to be screwed against plate 56 to precompress window assembly 30. In particular, as plate 56 presses against seal 40, it causes window 38 to press against seal 42, causing substantially equal precompression forces to be applied by seals 40 and 42 to surfaces 50 and 52, respectively, of window 38. However, because of the shape of window 38 and of the seals, most of the precompression force is in a direction normal to surfaces 50 and 52. This results in precompression of window 30 over substantially its entire volume. In particular, it results in precompression of the volume of the window between faces 46 and 48 in addition to precompression of the volume between the sealing rings. By contrast, for the prior art window assembly shown in FIG. 1, because of the direction in which precompression forces are applied, precompression of the quartz window occurs only for the portion of the window between the sealing rings and not for the portion of the window to which pressure 18 is applied. Window assembly 33 is similarly precompressed.

Since most of the forces applied to window 38 are compressive forces, irregularities in the window, seals or pressure plates merely result in variations in compressive stresses and not in shear stresses to the window. Since, as was previously indicated, quartz and the other materials utilized are substantially more resistant to compressive stresses than to shear stresses, this permits much larger precompression forces to be applied to the window without risking breakage thereof. Thus, the window assemblies may be precompressed so as to be able to operate with higher pressure differentials thereacross without inner seal 42 relaxing to the point where the seal fails.

Similarly, when chamber 24 is pressurized, the shear forces which would normally be caused by the pressure on the window and the resulting increased forces applied by seal 40 to window 38 are offset by the precompression of the window. Therefore, only when the pressure differential exceeds the precompression can shear stresses develop across the window. Since the design of the window assembly permits very high precompression forces to be applied to the window, the window assembly to be utilized in high pressure applications with at most minimal shear stresses, and thus without risk of shear stress failure. The window assemblies shown in FIGS. 2–4 can be designed so that the seal will fail as a result of seal 42 becoming fully relaxed beyond its precompression bias, thus limiting pressure buildup on the window, before the pressure applied to the window, is sufficient to cause shear stress failure of window 38.

Figure 5:
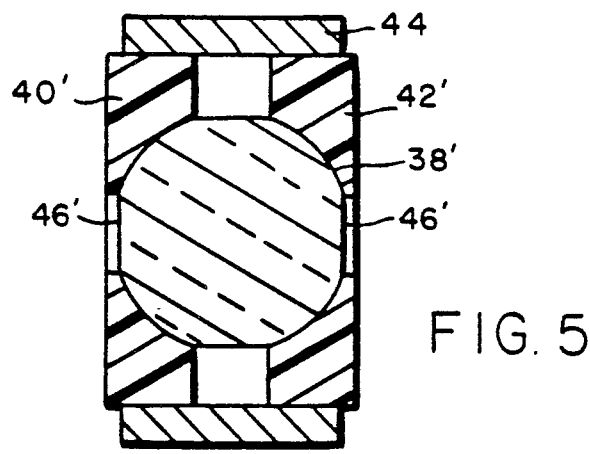
FIG. 5 is an enlarged cutaway side view of a single window assembly for an alternative embodiment of the invention.

From the above, it is apparent that the shape of window 38 to achieve the objectives of this invention should be designed such that forces applied to surfaces 50 and 52 are directed substantially toward the center of the window. While the preferred way to achieve this objection is as shown in FIGS. 2–4, with the surfaces 50 and 52 being at substantially a 45 degree angle to the faces 46 and 48, this objective may, to a lesser extent, be achieved as shown in FIG. 5 by having window 38' with an initially spherical shape and grinding or otherwise forming flat faces 46' and 48' on the sphere. The surfaces of sealing rings 40' and 42' in contact with window 38 would also preferably have rounded surfaces mating with the corresponding surfaces of window 38' so as to assure both a good seal and uniform transfer of forces to the window. Except for the difference in shape discussed above, the embodiment of FIG. 5 would function in substantially the same manner, and would provide most of the advantages of the embodiment previously discussed.

While the configurations shown in FIGS. 2–5 are preferred configurations for the window of this invention, there may be applications where, because of space limitations, cost, or other reasons, the shape of surfaces 50 and 52 might differ from the preferred. For example, the surfaces might be at a lesser angle than 45 degrees, might have a curve other than a pure circular curve, or might be formed of two or more shorter straight line segments, rather than a single segment as shown. All of these configurations will offer advantages over the configuration shown in FIG. 1 for the reasons discussed above, permitting more precompressive forces and thus less shear forces than the prior art, but will result in more shear forces than the configuration of the preferred embodiment. Further, while the surfaces 50 and 52 have been shown as being identical for the preferred embodiments, and this is clearly preferable for a number of reasons, this is not a requirement on the invention, and there may be applications where dissimilar angled surfaces are desirable.

Similarly, while for ease of manufacture and uniformity of force application, it is preferred that surfaces 46 and 48 and the remainder of the window have a circular shape, in some applications it may be desirable for other reasons that the window have other than a circular shape. The shape may, for example, be oblong or elliptical. However, it is preferable for uniform force distribution that the shape of surfaces 46 and 48 and of the remainder of the window not have any substantial corners.

In addition, while the preferred embodiment of the invention has been illustrated with respect to a chromatographic detector application, this is by no means a limitation on the invention and the window might find application in other ultra-high pressure applications where there is a requirement that some form of light radiation, whether infrared, visible or ultraviolet, be projected through the window. As previously indicated, light transmitting faces 46 and 48 are flat if the light is to be transmitted substantially undistorted and are appropriately curved to function as a lens if it is required that the light be focused. The manner of precompressing the window is also for purposes of illustration only and other forms of precompression known in the art might also be utilized. For example, screws might be provided with plates 60 which fit into suitable screw holes in housing 48.

Thus, while the invention has been particularly shown and described above with reference to preferred embodiments, the foregoing and other changes in form and detail may be made therein by one skilled in the art without departing from the spirit and scope of the invention.

What is claimed is:

1. A window assembly for transmitting a predetermined light radiation in applications where a substantial pressure differential exists between the environments separated by the window assembly comprising:

a window of a material which is substantially transparent to said light radiation, and which can withstand greater compressive stresses than shear stresses, said window having opposed surfaces oriented to permit said light radiation to pass therethrough, said opposed surfaces having a generally cornerless shape and having angled surfaces extending toward each other from corresponding points on outer edges of the opposed surfaces, each angled surface extending at a predetermined angle to the corresponding opposed surface;

a sealing ring bearing against each of said angled surfaces; and means for applying a precompression force to the sealing rings sufficient to normally maintain the window sealed when said pressure differential exists, said means also precompressing said window over portions thereof including portions between said opposed surfaces.

2. A window assembly as claimed in claim 1 wherein each of said opposed surfaces has a generally circular shape, and wherein each of said angled surfaces has a generally conical shape, with the conical shape being truncated at said opposed surface.

3. A window assembly as claimed in claim 2 wherein said angled surfaces do not meet, there being a short, generally cylindrical section of said window between the adjacent ends of said angled surfaces.

4. A window assembly as claimed in claim 1 wherein each of said sealing rings is formed with an angled surface which substantially matches the angled surface of the window in contact therewith, whereby sealing contact between the window and sealing ring is optimized.

5. A window assembly as claimed in claim 1 wherein the predetermined angle at which the angled surfaces extend from the opposed surfaces is substantially constant along the extent of each angled surface.

6. A window assembly as claimed in claim 5 wherein said predetermined angle is approximately 45°.

7. A window assembly as claimed in claim 1 wherein the predetermined angle at which the angled surfaces extend from the opposed surfaces change along the extent of each angled surface.

8. A window assembly as claimed in claim 7 wherein said window initially has a spherical shape with said opposed surfaces being formed on opposite sides of the spherical window, said angled surfaces being curved.

9. A window assembly as claimed in claim 1 wherein the predetermined angle at which the angled surfaces extend from the opposed surfaces is such that forces applied normal to the angled surface are directed substantially toward the center of the window.

10. A window assembly as claimed in claim 1 wherein said radiation is ultraviolet light, and wherein the material for said window is quartz.

11. A window assembly as claimed in claim 10 including a second like window assembly and a high pressure chamber of a chromatographic detector between said window assemblies, ultraviolet light entering the chamber through the window of one of said window assemblies and exiting the chamber to an ultraviolet light detector through the window of the other window assembly.

12. A window assembly as claimed in claim 1 wherein said means for applying a precompression force includes a plate bearing against one of said sealing rings, and means applying controlled pressure to the plate, thereby precompressing the rings.

13. A window assembly as claimed in claim 1 wherein said opposed surfaces are flat to transmit said light radiation substantially undistorted.

14. A window assembly as claimed in claim 1 wherein said opposed surfaces are curved to focus said light radiation.

15. A window assembly as claimed in claim 1 wherein the portions of said window which are precompressed comprise substantially the entire volume of the window.

* * * * *